United States Patent [19]

Shalaby et al.

[11] Patent Number: 4,689,424
[45] Date of Patent: Aug. 25, 1987

[54] RADIATION STERILIZABLE ABSORBABLE POLYMERIC MATERIALS AND METHODS FOR MANUFACTURING THE SAME

[75] Inventors: Shalaby W. Shalaby, Lebanon; Dennis D. Jamiolkowski, Long Valley, both of N.J.

[73] Assignee: Ethicon, Inc., Somerville, N.J.

[21] Appl. No.: 392,331

[22] Filed: Jun. 29, 1982

Related U.S. Application Data

[63] Continuation-in-part of Ser. No. 290,641, Aug. 6, 1981, Pat. No. 4,435,590.

[51] Int. Cl.[4] .............................................. C07C 69/76
[52] U.S. Cl. ...................................... 560/061; 528/176; 528/193; 528/194; 528/206; 128/334 C; 128/335.5
[58] Field of Search ................. 560/61; 528/176, 193, 528/194, 206; 128/334 C, 335.5

[56] References Cited

U.S. PATENT DOCUMENTS 2,516,955  8/1950  Butler ..................................... 560/61
4,518,763  5/1985  Barbee ................................. 528/176

Primary Examiner—Paul J. Killos
Attorney, Agent, or Firm—Charles J. Metz

[57] ABSTRACT

Radiation sterilizable polymeric materials, particularly radiation sterilizable absorbable, surgical products made from such polymeric materials.

34 Claims, No Drawings

RADIATION STERILIZABLE ABSORBABLE POLYMERIC MATERIALS AND METHODS FOR MANUFACTURING THE SAME

This application is a continuation-in-part of our application Ser. No. 290,641, filed Aug. 6, 1981 now U.S. Pat. No. 4,435,590.

The present invention relates to radiation sterilizable polymeric materials and, more particularly, to radiation sterilizable absorbable, surgical products made from such polymeric materials.

BACKGROUND OF THE INVENTION

For some years now, surgical devices, such as sutures, have been made from various synthetic absorbable materials. One example of such a synthetic absorbable suture is described in U.S. Pat. No. 3,297,033 issued Jan. 10, 1967, to Schmidt, et al., entitled "Surgical Sutures". Other examples of absorbable polymers which can be used to make surgical products are disclosed in U.S. Pat. Nos. 3,044,942, 3,371,069, 3,531,561, 3,636,956, RE 30,170 and 4,052,988.

Surgical devices such as sutures, protheses, implants and the like are usually sterilizable. In all of the prior art synthetic absorbable surgical devices, sterilizing may be accomplished by the normal use of heat or ethylene oxide sterilization or by other types of sterilization; however, it is believed that none of the prior art synthetic absorbable materials are, as a practical matter, sterilizable by radiation sterilization such as gamma radiation using a $^{60}$Co source. Some of the prior art indicates that synthetic absorbable material may be sterilized by irradiation or radiation, but we have found that radiation sterilization of the prior art synthetic absorbable materials at any practical usable level degrades the fabricated absorbable material to such an extent to render it unusable. The radiation sterilization of prior art synthetic absorbable sutures leads to distinct degradation in mechanical properties and to clinically unacceptable in vivo strength retention.

Three well accepted synthetic absorbable polymer materials which have been used to produce surgical devices, including sutures are polyglycolide, 10-90 poly(1-lactide-coglycolide) and poly-p-dioxanone. Tests have indicated that these products are only sterilizable by ethylene oxide, that radiation sterilization produces significant losses in both the physical and strength dependent biological properties of the material. These effects were discussed in an article written by Pitmann, et al. and appearing in the Journal of Polymer Science/Polymer Chemistry Edition, Volume 16, page 2722, 1978. Attempts to sterilize these polymers with more efficient and economical means, such as gamma radiation using a $^{60}$Co source, have proved impractical because of unacceptable deterioration in the tensile properties and in the in vivo performance of these polymers after gamma radiation. This is not unexpected if one recognizes the similarity in chemical structure between these polymers and the highly radiation sensitive polyoxymethylenes. Hence, the susceptibility of the molecular chains constituting these polymers are most likely to be highly radiation sensitive. Contrasted to this, poly(ethylene terephthalate), which is used to produce nonabsorbable surgical devices, is readily sterilized with gamma radiation using a $^{60}$Co source without significant loss in tensile properties. This is not surprising since the aromatic nature of the polymer chain is often associated with protection against gamma radiation degradation. It is believed that the poly(ethylene terephthlate) technology and the poly(lactide) technology have not been combined in an attempt to produce a hybrid material which may be absorbable yet stable against irradiation because of the diverse manner in which these polymers are made and the lack of common catalysts that can be used effectively in both types of polymerization. Additionally, at the high temperatures required for the synthesis of poly(ethylene terephthalate) the absorbable polylactones would undergo thermal degradation. Furthermore, it was believed that incorporating aromatic sequences in an absorbable chain could compromise the desirable physical and biological properties of an absorbable polymer.

In U.S. Pat. No. 2,516,955 there are disclosed some plasticized polymers. The plasticizers disclosed are esters of p-phenylene-dioxydiacetic acid. Low molecular weight polyesters of the latter acid are claimed to have been produced by Spanagel and Carouthers as reported in their article in the Journal of American Chemical Society, Vol. 57, pp. 935-936, 1935.

SUMMARY OF THE INVENTION

We have discovered new synthetic polymeric materials which may be sterilized by radiation while retaining desirable levels of physical and biological properties. In certain preferred embodiments of the invention, the radiation sterilizable synthetic polymers are absorbable polymers and are used to produce sterile, absorbable, surgical devices such as sutures, sutures with attached needles, molded devices, and the like. The invention also contemplates various new and improved processes for producing radiation sterilizable, absorbable homopolymers and copolymers. Furthermore, we have discovered new methods for producing the new monomers of the invention used in the preparation of certain of the new polymers of the invention. Our new polymers are sterilizable using radiation and provide all the economic and safety advantages inherent with radiation sterilizing processes. The new radiation sterilizable absorbable compositions of the invention comprise polymers containing units of Formula I:

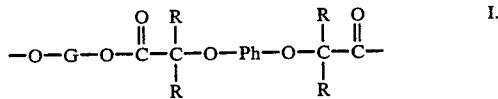

where G represents the residue minus the hydroxyl groups of a dihydric alcohol, wherein each R individually represents hydrogen or alkyl, and wherein Ph represents 1,2-, 1,3-, or 1,4-phenylene.

There are several types of polymers contemplated by the invention. One type comprises "homopolymers" consisting essentially of recurring units of Formula I. Such polymers are produced by reacting a phenylene-bis-oxyacetate (or the corresponding diacid) with a dihydric alcohol. Said phenylene-bis-oxyacetates are represented by Formula II:

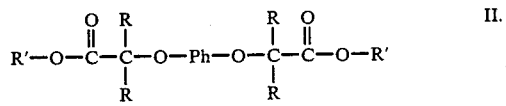

wherein Ph and R are as defined above with respect to Formula I, and wherein each R' individually represents lower alkyl or phenyl.

Typically, the bis-oxyacetate is reacted with a diol such as ethylene glycol, in the presence of a suitable catalyst and at an elevated temperature of from, for example, about 120° C. to 220° C. and in an inert atmosphere such as nitrogen to produce a low molecular weight polymer. The low molecular weight polymer is then heated to an elevated temperature, e.g., about 190° C. to 240° C., while reducing the pressure to about 5 mm. of mercury or less to continue the reaction and produce a higher molecular weight polymer having an inherent viscosity of at least 0.1 dl/g measured at 25° C. at a concentration of 0.1 g/dl in hexafluoroisopropyl alcohol. Further increase in the degree of polymerization can be achieved by solid state post polymerization or ground crystalline polymer below its melting temperature but not less than about 80° C., preferably under a vacuum.

The preferred dialkyl phenylene-bis-oxyacetate used in producing the polymers of the present invention is our new monomer (dimethyl phenylene-bis-oxyacetate) which is an easily purified, easily crystallized monomer capable of being polymerized to produce high molecular weight polymers having an inherent viscosity of greater than 0.3 dl/g measured at 25° C. at a concentration of 0.1 g/dl in hexafluoroisopropyl alcohol.

It is preferred that our new monomer (dimethyl phenylene-bis-oxyacetate) be produced using our new method of reacting hydroquinone with methyl chloroacetate and a metal alkoxide, preferably sodium methoxide, in a mole ratio of 1:2:2 respectively, in methanol at the reflux temperature of the mixture and in the absence of oxygen for a sufficient period of time to dietherify the hydroquinone at yields of 50% or greater. A modified process for producing our new monomers is to substitute potassium carbonate for the sodium methoxide and to carry out the reaction in acetone at the reflux temperature of the mixture. The high-energy radiation sterilizable surgical devices of the present invention may be made from various copolymers incorporating units represented by Formula I along with lactide and/or glycolide units. Such copolymers are represented by Formula III:

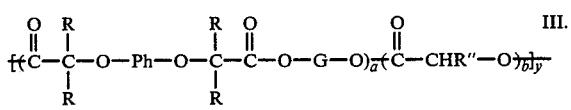

wherein G, R, and Ph are as defined above with respect to Formula I, wherein R" represents hydrogen or methyl, wherein a and b are numbers whose average values represent the proportion in the copolymer of the units represented by Formula I (which will be referred to herein as the phenylene-bis-oxyacetate units) and the glycolide and/or lactide units, respectively, and wherein y is a number whose average value represents the degree of polymerization of the polymer.

These new copolymers may be produced by reacting a mixture of glycolide and/or lactide, phenylene-bis-oxyacetate as described above, and dihydric alcohol in the presence of a suitable catalyst, at an elevated temperature of, for example, from about 120° C. to 240° C. under an inert atmosphere such as nitrogen, followed by reacting the mixture at an elevated temperature of, for example, from about 160° C. to 240° C. and under a reduced pressure of less than 5 mm. for a sufficient period of time to produce a solid polymer having an inherent viscosity of at least 0.3 dl/g measured at 25° C. at a concentration of 0.1 g/dl in hexafluoroisopropyl alcohol.

The polymers of Formula III can also be produced by reacting a polymer consisting essentially of recurring units of Formula I with a glycolide and/or a lactide with or without a hydroxylic molecular weight regulator, at an elevated temperature, preferably either less than 205° C. or greater than 215° C. for a period of time sufficient to produce a solid polymer material having an inherent viscosity of at least 0.3 dl/g measured at 25° C. at a concentration of 0.1 g/dl in hexaflouroisopropyl alcohol.

Other new copolymers of the invention made from phenylene-bis-oxyacetate or suitable derivatives have the following Formula IV:

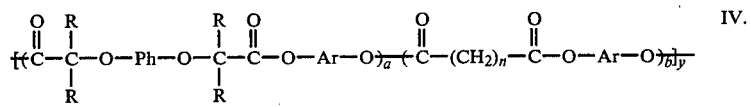

wherein Ar represents 1,3- or 1,4-phenylene, wherein Ph and R are as defined above with respect to Formula I, wherein n is a number having an average value of from 4 to 10, wherein a and b are numbers whose average values reflect the proportions of the two components of the polymer, and y is a number whose average value reflects the degree of polymerization resulting in a solid polymer having an inherent viscosity of at least 0.3 dl/g measured at 25° C. at a concentration of 0.1 g/dl in hexafluoroisopropyl alcohol. These new high-energy radiation sterilizable random copolymers may be produced by reacting a phenylene-bis-oxyacetic acid or ester thereof with an aliphatic di-acid or mixtures thereof, with a hydroquinone or a resorcinol diester in the presence of a suitable catalyst and at an elevated temperature, e.g., of from 200° C. to 280° C. for a sufficient period of time to produce a solid polymer having an inherent viscosity of at least 0.3 dl/g measured at 25° C. at a concentration of 0.1 g/dl in hexafluoroisopropyl alcohol.

DETAILED DESCRIPTION OF THE INVENTION

Preparation of Monomer

Our new monomer is the preferred monomer used in producing the new polymers of the invention and is of the formula:

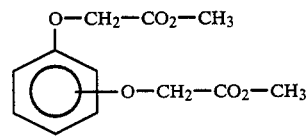

where the benzene ring is 1,2-, 1,3-, or 1,4-substituted. The methyl ester monomer has the advantages of being easily purified and easily crystallized. By being readily purifiable and crystallizable, the monomers may be polymerized to produce high molecular weight polymeric materials with good yields and good purity which is important in producing surgical devices. As previously pointed out, the para and meta forms of phenylene diglycolic acids are knonw as is diethyl phenylene-bis-oxyacetate and were claimed to be produced by Spanagel and Carouthers as previously mentioned. The polymers described by Spanagel and Carouthers were viscous resins and obviously were not of high molecular weight and could not be used to make radiation sterilizable, absorbable, surgical devices. When polymerizing the acid, as it is believed was done by Spanagel and Carouthers, the resultant polymer was not of a sufficiently high molecular weight to be useful in producing surgical devices. In the prior art, the diesters were produced by reacting hydroquinone with chloroacetic acid in the presence of sodium hydroxide to produce the diacid which is to be esterified by a standard esterification. This procedure is tedious and produces esters which require numerous recrystallizations to produce material of sufficient purity for polymerization. Our new monomer is produced in relatively high yield following a one step reaction wherein hydroquinone is reacted with methyl chloroacetate and sodium methoxide in the presence of methanol. Yields with respect to the hydroquinone are improved when the methyl chloroacetate and sodium methoxide ae used in stoichiometric excess. The reaction is carried out at the reflux temperature of the mixture. The following is a specific example of our new method for producing the new monomer:

EXAMPLE 1

A dry 5 liter, 3-neck round bottom flask equipped with an additional funnel with a nitrogen inlet, a mechanical stirrer, and a reflux condenser with drying tube, a thermometer and a heating mantle is charged with 330.3 grams (3 moles) of hydroquinone, 651.1 grams (6 moles) of methyl chloroacetate, and 1722 ml. of methanol. The contents of the flask are brought to reflux (approximately 68° C.) after an initial purge with nitrogen. A solution of sodium methoxide in methanol (1182 grams, 27.4 weight percent or 6 moles of sodium methoxide), is charged to the addition funnel and allowed to slowly enter the refluxing reaction solution over the course of approximately one hour.

After the addition is completed, the reaction mixture is allowed to reflux an additional 17 hours during which time the reflux temperature drops to 65° C. The solution is filtered while hot (above 60° C.) to remove the sodium chloride. The filtrate is cooled and a white crystalline material precipitates. The crystals are filtered and a dry weight of 498.9 grams is obtained. The crystals are twice re-crystallized from methanol using 4 ml of methanol per gram of dry weight of crystals to result in dimethyl phenylene-bis-oxyacetate having a melting point of 99°–101° C. and with an overall yield of at least 55.4%.

CONTROL EXAMPLE 2

As a comparison to our new process, the dimethyl phenylene-bis-oxyacetate is prepared by the process analagous to that of the prior art. A 5 liter, 3-neck round bottom flask is charged with chilled aqueous solution of chloroacetic acid, (581.1 grams (6.15 moles) and 450 ml. of water) followed by the careful addition of a chilled aqueous sodium hydroxide solution, (246 grams (6.15 moles base) and 450 ml. of water). The flask is outfitted with a reflux condenser, an addition funnel, a thermometer and a heating mantle. To a separate flask containing a chilled aqueous sodium hydroxide solution, (204 grams sodium hydroxide (6 moles of base) and 900 ml. of water) is carefully and slowly added 330.3 grams (3 moles) of hydroquinone. The temperature is moderated by external cooling. The second solution is charged to the additional funnel of the first flask. With the contents of the round bottom flask being stirred vigorously, the hydroquinone solution is allowed to enter while heating the flask to 100° C. When 100° C. is attained the mantle is shut down and a concentrated aqueous hydrochloric acid solution of 37% hydrochloric acid, 640 ml. (7.7 moles) is carefully but quickly added. The solution is allowed to cool to room temperature. The precipitated crystals of diacid are filtered, washed 3 times with chilled water and dried. Four hundred fifty grams, 63% yield of p-phenylene-bis-oxyacetic acid is obtained. The crude diacid is converted to the corresponding dimethyl ester in the following manner: 450 grams of the dry diacid is charged to a 5 liter, single neck round bottom flask along with 2500 ml. of methanol, 450 ml. of carbon tetrachloride and 7 grams of p-toluene sufonic acid along with a magnetic spin bar. The flask is outfitted with a Dean-Stark trap with a bottom stopcock outlet, a reflux condenser and a heating mantle. The mixture is refluxed for 19 hours after which time a portion of the solvents, 700 ml., are removed through the bottom outlet of the Dean-Stark trap. The solution is filtered hot and the filtrate allowed to cool slowly with stirring to precipitate the diester. The mixture is cooled at below room temperature to complete crystallization and the crystals filtered, washed with chilled methanol and dried in a vacuum at room temperature. Four hundred grams of dimethyl p-phenylene-bis-oxyacetate are obtained. The diester is recrystallized 3 times from isopropanol using 4 ml. of isopropanol per gram of material and employing activated charcoal to remove the color and produce the diester. The diester has a melting point of 99°–101° C. and 280 grams are produced providing an overall yield of 36.7%.

Comparing Examples 1 and 2, it can be seen that our new process for producing the monomer has a greater yield than the prior art process. Furthermore, our new process is a simpler process in that it is accomplished in one reaction step rather than the two reaction steps of the prior art. Furthermore, our new process produces a more readily crystallizable and purifiable material which can be easily polymerized in accordance with the present invention. Our new process may be used to produce the ethyl ester as well, though the ethyl ester is not nearly as suitable as is the methyl ester in producing the new polymers of the invention. The ethyl ester is not as easy to purify as the methyl ester, and perhaps more importantly, is not as reactive as the methyl ester, especially at low catalyst concentrations. The fact that the methyl ester is very reactive at low catalyst concentrations is important in order to be able to produce many of the desirable copolymers in accordance with the invention.

An alternate process for producing our new monomers is to substitute potassium carbonate for the sodium methoxide and to substitute acetone for the methanol and to carry out the reaction in all other aspects as described above with the exception of refluxing at the boiling temperature of acetone. This technique also produces a very pure material with good crystallizability at yields of greater than 50%. The following is an example of this alternate process.

EXAMPLE 3

A mixture consisting of 55.0 g. (0.5 mole) of hydroquinone, 108.5 g. (1.0 mole) methyl chloroacetate, 138.2 g. (1.0 mole) anhydrous potassium carbonate, 10 g. (0.06 mole) of potassium iodide and 500 ml. of dry acetone are stirred and refluxed under nitrogen for 48 hours. The mixture is filtered and the solid extracted with one liter of hot acetone. The original filtrate and the acetone extract are combined and evaporated to dryness. A residue (124 grams) containing some methyl chloroacetate is removed by trituration with one liter of ether. After filtration there remains 100.8 g. (79.3%) of a gray-pink product (m.p. 96°–99° C.). Recrystallization of the crude material from one liter of absolute methanol yields 82.8 g. and after reduction of the filtrate to one-half volume and decolorization with Darco an additional 5.7 g. of dimethyl p-phenylene-bis-oxyacetate. The total yield is 88.5 g. (69.6% amounting to 87.8% recovery after the recrystallization) of an off-white material, m.p. 98°–99° C.

PREPARATION OF THE HOMOPOLYMER

The "homopolymers" of the invention are poly(phenylene-bis-oxyacetates) of the formula:

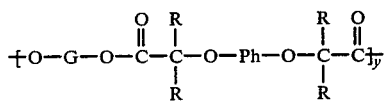

VI.

wherein G, R, and Ph are as described above with respect to Formula I, and wherein y is a number whose average value reflects the degree of polymerization.

Our new homopolymers are preferably crystalline materials having molecular weights in excess of 5000 and having an inherent viscosity of at least 0.1 dl/g. As previously mentioned, when Spanagel and Carouthers attempted to make the poly(alkylene-phenylene bis-oxyacetate) polymers, with their monomers they produced brown viscous materials which indicates they did not make the crystallizable, purifiable monomers of the present invention and, hence, could not produce the high molecular weight homopolymers of the present invention.

These polymers are produced by reacting a phenylene-bis-oxyacetic acid or (preferably) diester thereof with a dihydric alcohol in the presence of a small catalytic amount of a suitable catalyst such as dibutyltin oxide or stannous octoate. The preferred phenylene reactant is dimethyl p-phenylene-bis-oxyacetate. Other phenylene reactants include diphenyl p-phenylene-bis-oxyacetate, dimethyl m-phenylene-bis-oxyacetate, dimethyl o-phenylene-bis-oxyacetate, dimethyl p-phenylene-bis-(2-oxypropionate), dimethyl p-phenylene-bis-(oxy-2,2-dimethylacetate), diethyl-p-phenylene-bis-oxyacetate, their ring-alkylated derivatives, mixtures thereof, and the like. Illustrative dihydric alcohols, which can be used alone or in mixtures thereof, include: $C_2$ to $C_{16}$ alkylene glycols such as ethylene glycol, 1,2- and 1,3-propylene glycol, 1,4-butylene glycol, 1,6-hexylene glycol, and the like; polyalkylene glycols such as diethylene glycol, triethylene glycol, poly(oxytetramethylene) glycol, and the like; cycloaliphatic diols such as 1,4-cyclohexanedimethanol, and the like; and aromatic dihydric alcohols such as 1,4-bis(2-hydroxyethoxy)benzene, and the like.

The following are specific examples of the production of the homopolymers of the invention.

EXAMPLE 4

To a flame dried, mechanically stirred, 1 liter glass reactor, suitable for polycondensation reactions, is charged 127.1 grams of dimethyl 1,4-phenylene-bis-oxyacetate (0.5 moles), 62.1 grams ethylene glycol (1.0 mole) and 9.0 milligrams dibutyltin oxide (0.0071 weight percent based on the expected polymer weight). After purging the reactor and venting with nitrogen the reactor is immersed in a silicone oil bath and connected to a gas supply to maintain nitrogen at 1 atmosphere of pressure. The stirred mixture is heated to and maintained at 160° C., 190° C. and 210° C. for 2, 1 and 2 hours respectively during which time the methanol along with some ethylene glycol is collected. The reactor is allowed to cool to room temperature. Some time later the reactor is evacuated and heated; temperatures of 190° C., 210° C. and 220° C. are maintained for 1, 1, and 2 hours respectively. The collection of distillate is continued during the low pressure (less than about 100 microns) stage of the polymerization. The temperature is increased from 220° C. to 240° C. over the course of 30 minutes and 240° C. is maintained for 3 hours. The reactor is removed from the oil bath and allowed to cool. The formed polymer is isolated, ground and dried. The polymer has an inherent viscosity of 1.31 dl/g as determined in hydrofluroisopropyl alcohol at 25° C. and a concentration of 0.1 g/dl.

Lower molecular weight polymers can be easily produced by decreasing the reaction time at 240° C. or by decreasing the final polymerization temperature. These techniques are well known to those skilled in the art of polycondensation reactions.

The polymers may also be produced in a three stage polymerization where the diacid moiety, the diol, and a catalyst are heated at atmospheric temperatures (under nitrogen) in a molten state, followed by reaction at reduced pressure in a molten state to produce relatively low molecular weight species of the polymer. The low molecular weight material is pelletized or ground and crystallized. The material is heated under vacuum in a third stage at a temperature below its melting point. This last solid stage polymerization stage increases the molecular weight significantly.

EXAMPLE 5

To a flame dried, mechanically stirred, 250 ml reactor, suitable for polycondensation, is charged 60.0 grams of dimethyl 1,4-phenylene-bis-oxyacetate (0.236 mole), 31.6 grams ethylene glycol (0.509 mole) and 11.7 milligrams of dibutyltin oxide (0.0197 weight percent based on expected polymer weight). After purging the reactor and venting with nitrogen, the reactor is immersed in a silicone oil bath and further connected to a gas supply to maintain nitrogen at one atmosphere of pressure. The stirred mixture is heated to and maintained at 190° C. for 7 hours during which time the formed methanol, along with some ethylene glycol is collected. the pressure in the reactor is reduced and a temperature of 190° C. maintained for an additional 3 hours under high vacuum. The stirred reaction mass is maintained under vacuum at 200° C. and 220° C. for 2 and 7 hours respectively while continuing to remove distillates. The polymer is subjected to 100° C. for 3 hours during which time the polymer crystallizes. The polymer is isolated, ground (particle size less than 3 mm) and dried. The polymer has an inherent viscosity of 0.76 dl/g measured in hydrofluoroisopropyl alcohol at 25° C. and a concentration of 0.1 g/dl.

The finely divided crystalline polymer is charged to a dry round bottom flask. The pressure in the flask is reduced below about 100 microns and the flask immersed in a silicone oil bath at 135° C. for a total of 34 hours. The inherent viscosity of the polymer increases to 1.04 dl/g.

The para-isomer of our new homopolymer is especially suitable for producing fiber forming polymers and surgical sutures.

EXAMPLE 6

The polymer of Example 5 is extruded at 160° C. using an Instron Capillary Rheometer employing a 40 mil die and a shear rate of 213 sec$^{-1}$. The melt viscosity at this temperature is determined to be 3600 poise. The extrudate is drawn in a glycerine draw bath in two stages: 6 times at 52° C. followed by 1.5 times at 90° C. The diameter, straight tensile strength, and the elongation at break of the monofilament are determined to be 5.8 mil; 89,700 PSI; and 24% respectively. The monofilament is subsequently annealed under tension at 65° C. for 16 hours. The diameter, straight and knot tensile strengths, the elongation at break, and the modulus are determined to be for the annealed monofilament: 5.7 mil; 92,400 PSI; 75,000 PSI; 26% and 2.4 million PSI respectively.

EXAMPLE 7

Monofilament fiber made from poly(ethylene 1,4-phenylene-bis-oxyacetate) is sterilized with a dosage of 2.5 Mrads of gamma radiation using a $^{60}$Co source. The breaking strength, straight tensile strength, elongation at break and diameter of the monofilament are measured before and after the sterilization. The results are as follows:

|  | Initial | After a Dose of 2.5 Mrads |
| --- | --- | --- |
| Breaking strength (Lbs.) | 1.75 | 1.49 |
| Straight tensile strength (psi) | 52,700 | 43,500 |
| Elongation at break (%) | 47 | 33 |
| Diameter (mils) | 6.5 | 6.6 |

EXAMPLE 8

A flame dried, mechanically stirred 1000 ml glass reactor (suitable for polycondensation reactions) is charged with 127.1 g of dimethyl 1,4-phenylene-bis-oxyacetate (0.50 moles) and 75.7 g of trans 1,4-cyclohexanedimethanol (0.525 moles) and 9.0 milligrams of dibutyltin oxide (0.036 millimoles, 0.0054 weight percent of expected polymer weight. After purging the reactor and venting with nitrogen the reactor is immersed in a silicone oil bath and further connected to a gas supply to maintain nitrogen at one atmosphere of pressure. The stirred mixture is heated to and maintained at 160° C., 190° C., and 230° C. for 2, 1, and 2 hours respectively during which time the formed methanol is collected. The reactor is allowed to cool to room temperature overnight. The next day the pressure is reduced to about 100 microns of mercury and the vessel reheated to and maintained at 190° C., 210° C., 220° C. and 240° C. for 1, 1, 3, and 1.5 hours respectively to continue the polycondensation process. During this time the distillates are collected. The polymer is isolated, ground and dried under vacuum at room temperature. The inherent viscosity of the resulting polymer is approximately 0.93 dl/g measured at 25° C. at a 0.1 g/dl concentration in hexafluoroisopropyl alcohol. In a companion experiment the polymerization as described in this Example 8 is carried out substituting 72.5 grams of para-phenylene dimethanol (0.525 moles) for the trans 1,4-cyclohexanedimethanol. A similar polymer is obtained.

EXAMPLE 9

A flame dried, mechanically stirred 1000 ml. glass reactor (suitable for polycondensation reactions) is charged with 127.1 g of dimethyl 1,4-phenylene-bis-oxyacetate (0.500 mole), 76.8 g, 1,8-octanediol (0.525 mole) and 9.0 milligrams of dibutyltin oxide (0.036 millimoles, 0.0054 weight percent of expected polymer weight). The reactor is purged and vented with nitrogen and immersed in a silicone oil bath. The reactor is connected to a gas supply to maintain nitrogen at one atmosphere of pressure. The stirred mixture is heated to and maintained at 160° C., 190° C., and 210° C. for 2, 1, and 2 hours respectively during which time the formed methanol is collected. The reactor is allowed to cool to room temperature overnight. The next day the pressure is reduced to about 100 micron of mercury and the reactor reheated to and maintained at 190° C., 210° C., 220° C., and 240° C. for 1, 1, 2, and 2 hours, respectively to continue the polycondensation process. During this time the distillates are collected. The polymer is isolated, ground and dried under vacuum at room temperature. The inherent viscosity of the polymer is 0.78 dl/g measured at 25° C. at a 0.1 g/dl concentration in hexafluoroisopropyl alcohol.

EXAMPLE 10

A frame dried, mechanically stirred 500 ml glass reactor (suitable for polycondensation reactions) is charged with 89.0 grams of dimethyl 1,3-phenylene-bis-oxyacetate (0.35 moles), 43.4 grams ethylene glycol (0.70 moles) and 6.3 milligrams dibutyltin oxide (0.025 millimoles, 0.0071 weight percent based on the expected polymer weight). The reactor is purged and vented with nitrogen and immersed in a silicone oil bath. The immersed reactor is connected to a gas supply to maintain nitrogen at one atmosphere of pressure. The stirred mixture is heated to and maintained at 160° C., 190° C., and 210° C. for 2, 1, and 2 hours respectively, during which time the formed methanol is collected. The reactor is allowed to cool to room temperature overnight. The next day the pressure is reduced to about 100 microns of mercury and the vessel reheated to and maintained at 190° C., 210° C., and 220° C. for 1, 2, and 6 hours respectively. During this time the distillates are collected. The polymer is isolated, ground and dried under vacuum at room temperature. The inherent viscosity of the polymer is approximately 0.84 dl/g measured at 25° C. at a concentration of 0.1 g/dl in hexafluoroisopropyl alcohol.

Though the ortho isomer of our poly(phenylene-bis-oxyacetate) polymers cannot generally be used to produce fiber type surgical devices, it is thermoplastic and a solid polymer of a molecular weight of at least 5000 and of an inherent viscosity of at least 0.1 dl/g can be produced. The meta form, though fiber forming, usually produces dimensionally unstable fibers because of little or no crystallinity of the polymer. However, the meta form of the polymer can be shaped and molded by conventional techniques to produce useful high-energy radiation sterilizable surgical products.

In view of the chemical structure of our new homopolymer, it would be expected that the ether bonded to the ring would be flexible, and that a low modulus material would therefore be produced. Surprisingly and unexpectedly, we have found that our new homopolymer materials have high modulus in spite of the ether linkages, as may be seen in Examples 6 and 7.

It may be theorized that the high modulus material results from a liquid crystalline morphology of our material which provides a high degree of chain orientation that is associated with an anisotropic melt. This is especially true of the para form of our new polymer which is sufficiently anisotropic and can be spun into fine diameter materials. It is very strong and may be used for various surgical devices such as artificial tendons and the like. Our new homopolymers are sterilizable using high energy radiation; such as gamma irradiation using a Cobalt 60 source.

PREPARATION OF COPOLYMERS WITH GLYCOLIDE

The first type of copolymer contemplated by the invention are those that are produced by reacting a phenylene-bis-acetic acid (or, preferably, diester), a dihydric alcohol, and glycolide and/or lactide. These copolymers are represented by Formula III, above. The bis-phenylene compounds and the diols that are used to produce the homopolymer are also the ones used to produce this copolymer. The discussion above concerning these reactants is also applicable here.

In certain aspects of the invention, the proportion of glycolide and/or lactide in the copolymer is important. For instance, when the copolymer is being made directly from the monomers, when the proportion of lactide and/or glycolide residue in the polymer exceeds about 20 weight percent, the polymer is less useful for fiber-forming applications because the temperature at which the oriented polymer relaxes and begins to lose orientation begins to approach ambient temperatures. Such polymers can be used to make molded articles, and the like, but are not preferred for fibrous applications such as sutures.

The following examples illustrate the production of these copolymers:

EXAMPLE 11

A flame dried, mechanically stirred 250 ml glass reactor suitable for polycondensation reactions is charged with 25.0 grams of dimethyl 1,4-phenylene-bis-oxyacetate (0.0983 moles), 13.2 grams ethylene glycol (0.213 moles), 2.17 grams glycolide (0.0187 moles) and 9.7 milligrams dibutyltin oxide (0.036 weight percent based on expected polymer weight). After purging the reactor and venting with nitrogen, the reactor is immersed in a silicone oil bath and further connected to a gas supply to maintain nitrogen at one atmosphere pressure. The stirred mixture is heated to and maintained at 180° C. for 7 hours during which time the formed methanol is collected. The reactor is allowed to cool to room temperature, some time thereafter the reactor is evacuated and reheated; temperatures of 180° C., 190° C., and 200° C. are maintained for 2, 0.5, 8 hours respectively. During this low pressure (less than 100 microns) stage of the polymerization, the collection of distillates is continued. The temperature is reduced to and maintained at 80° C. for 3 hours to crystallize the polymer sample. The oil temperature is brought up to 130° C. and maintained for 4 hours to anneal the bulk resin. The polymer is isolated, ground and dried. The polymer has an inherent viscosity of 0.60 dl/g. The finely divided polymer is charged to a round bottom flask. The pressure in the flask is reduced below about 100 microns; the flask immersed in a silicone oil bath at 80° C. and 135° C. for 2 and 41 hours respectively. The inherent viscosity of the resulting polymer is 1.22 dl/g. The copolymer exhibited a major endothermic transition at 159° C. (DSC; 20° C./min) and 30% crystallinity as measured by X-ray techniques. The resultant polymer comprises approximately 16 mole percent (8 weight percent) of glycolide moieties.

EXAMPLE 12

A flame dried 500 ml glass reactor mechanically stirred and suitable for polycondensation reactions is charged under dry, oxygen-free conditions with 63.6 g. dimethyl 1,4-phenylene-bis-oxyacetate (0.250 moles), 41.7 g. of trans 1,4-cyclohexanedimethanol (0.289 moles), 1.53 g. glycolide (0.0132 moles) and 6.2 milligrams dibutyltin oxide (0.025 millimoles, 0.0073 weight percent of expected polymer weight). The reactor is purged and vented with nitrogen and immersed in a silicon oil bath. The immersed reactor is connected to a nitrogen supply to maintain one atmosphere of pressure. The stirred mixture is heated to and maintained at 160° C., 190° C., and 210° C. for 2, 1, and 3 hours respectively during which time the formed methanol is collected. The reactor is allowed to cool to room temperature overnight. The next day the pressure is reduced to about 100 microns of mercury and the vessel reheated to and maintained at 190° C., 210° C., and 220° C. for 1, 1, and 7 hours respectively to continue the polymerization. The distillates are collected during the polymerization. The polymer is isolated, ground and dried under vacuum at room temperature. The inherent viscosity of the polymer is approximately 1.07 g/dl. The resultant polymer comprises approximately 5.0 mole percent (1.8 weight percent) of glycolide moieties.

EXAMPLE 13

A flame dried, mechanically stirred 500 ml glass reactor suitable for polycondensation reactions, is charged under dry, oxygen-free conditions with 76.3 g. of dimethyl 1,4-phenylene-bis-oxyacetate (0.300 mole), 27.9 g. ethylene glycol (0.449 mole), 23.2 g. glycolide (0.200 mole), and 6.2 mg. dibutyltin oxide (0.025 millimoles, 0.0063 weight percent of the expected polymer weight). The reactor is purged and vented with nitrogen and immersed in a silicon oil bath. The immersed reactor is connected to a gas supply to maintain nitrogen at one atmosphere of pressure. The stirred mixture is heated to and maintained at 160° C., 190° C., and 210° C. for 2, 1, and 2 hours respectively during which time the formed methanol is collected. The reactor is allowed to cool to room temperature overnight. The next day the pressure is reduced to about 100 microns of mercury and the vessel reheated to and maintained at 190° C., 210° C., and 220° C. for 1, 1, and 6 hours respectively. During this time the distillates are collected. The polymer is isolated, ground and dried under vacuum at room temperature. The resultant polymer comprises 40 mole percent of glycolide moieties (23.5 weight percent) and has an inherent viscosity of approximately 1.33 dl/g.

EXAMPLE 14

A flame dried, mechanically stirred 100 ml glass reactor, suitable for polycondensation reactions, is charged with 25.0 grams dimethyl 1,4-phenylene-bis-oxyacetate (0.0983 moles), 12.2 grams ethylene glycol (0.197 moles), 1.56 grams glycolide (0.0134 moles) and 4.9 milligrams of dibutyltin oxide (0.019 weight percent of the expected polymer weight). The reactor is purged and vented with nitrogen. The reactor is immersed in a silicone oil bath. The immersed reactor is connected to a gas supply to maintain nitrogen at a pressure of one atmosphere. The stirred mixture is heated to and maintained at 180° C. for 7 hours during which time the formed methanol is collected. The reactor is allowed to cool to room temperature. The reactor is reheated to 230° C. under nitrogen to continue the polymerization and remove some excess ethylene glycol. The temperature is lowered to 200° C. and the pressure reduced. Temperatures of 200° C., 220° C., and 240° C. are maintained for 0.5, 1.5, and 2 hours respectively while continuing to remove distillates under reduced pressure. The polymer is isolated, ground and dried under vacuum at room temperature. The polymer comprises approximately 12 mole percent (5.9 weight percent) of glycolide moieties. The inherent viscosity of the polymer is determined to be 0.95 dl/g. Thermal microscopy of the bulk polymer reveals a melting transition below 140° C. The polymer is extruded using an Instron Capillary Rheometer through a 40 mil die at 160° C. and a shear rate of 213 sec$^{-1}$. The melt viscosity at this temperature is 2,200 poises. The fiber is taken up through ice water and subsequently drawn in two stages using a glycerine draw bath at draw ratios of 8 times at 53° C. followed by 1.25 times at 65° C. The two-stage drawn fiber is annealed under tension at 63° C. for 2 hours.

The following table summarizes the physical property data obtained on the drawn fiber prior to and after annealing and after exposure to a 2.5 Mrad dose of gamma radiation.

TABLE

| | Prior to Annealing | After Annealing | After Annealing & gamma radiation |
|---|---|---|---|
| Diameter (mil) | 5.4 | 5.5 | 5.5 |
| Straight Tensile Strength (psi) | 42,900 | 44,300 | 44,700 |
| Knot Tensile Strength (psi) | 40,300 | 40,500 | 38,200 |
| Elongation at Break (%) | 55 | 40 | 40 |
| Young Modulus (10 psi) | 1.06 | 1.59 | 1.51 |

PREPARATION OF COPOLYMERS BY REACTING HOMOPOLYMER WITH GLYCOLIDE

The second type of copolymer is produced by reacting the homopolymer of Formula VI with glycolide and/or lactide in the presence of a suitable catalyst. This copolymer is also represented by Formula III. The following examples illustrate the production of the copolymers by this procedure.

EXAMPLE 15

A flame dried 1,000 ml. round bottom flask outfitted with a vacuum tight, stainless steel, mechanical stirrer and a hose connection is charged under dry, oxygen-free, conditions with 313.4 grams (2.7 moles) of glycolide and 75.7 grams of finely divided (passing a 10 mesh screen) amorphous, dry poly(ethylene 1,4-phenylene-bis-oxyacetate) resin, prepared in the presence of 0.01974 weight percent of dibutyltin oxide as a catalyst to an inherent viscosity of 0.63 dl/g. The reactor is purged and vented with nitrogen and immersed in a silicone oil bath and connected to a gaseous supply to maintain nitrogen at a pressure of one atmosphere. The mixture is heated for about one-half hour using a bath temperature of 120° C. to melt the glycolide and start the dissolution of the polyester. The temperature is increased at the rate of 1.8° C. per minute to 150° C. which is maintained for 8 minutes to continue the dissolution process. The heating bath is brought up in temperature to 195° C. at an average rate of 1.5° C. per minute. Stirring is discontinued prior to reaching 195° C. because of the viscous nature of the reaction mass. The forming polymer crystallizes and is maintained at 195° C. for 8 hours. The polymer is isolated, ground and dried under vacuum at room temperature overnight. Some unreacted glycolide is removed by heating the ground polymer to 110° C. at 0.1 mm. mercury for 16 hours. About a 0.2% weight loss is observed indicating a high degree of conversion. The ground polymer is sieved to remove particles less than 1 mm. in diameter. Two hundred twenty-five grams of the polymer free from fines is produced. Samples of the polymer are analyzed and NMR data indicate the chemical structure of the polymer to be that of the copolymer of Formula III, above. The NMR data indicates the copolymer comprises 89.5 mole percent (79.7 weight percent) of the glycolide moieties and 10.5 mole percent (20.3 weight percent) of the poly(ethylene 1,4-phenylene-bis-oxyacetate) moieties. The inherent viscosity of the polymer after prolonged heating at 50° C. to dissolve the polymer is found to be 1.69 dl/g.

EXAMPLE 16

A 100 ml flame dried stirred reactor is charged with 7.8 grams dry, amorphous, finely divided poly(ethylene 1,4-phenylene-bis-oxyacetate) (prepared in the presence of 0.02 weight percent dibutyltin oxide; inherent viscosity 0.91 dl/g), 29.0 grams glycolide (0.250 moles), 4.0 grams L(−) lactide (0.028 moles) and 10.5 milligrams glycolic acid (0.138 millimoles). After purging the reactor it is vented with nitrogen which is maintained at a pressure of one atmosphere for the remainder of the polymerization. The vessel is immersed in a silicone oil bath and heated to 105° C. to melt the glycolide and start the dissolution of the polyester resin. The temperature is raised to 120° C. to continue and complete the dissolution process. The temperature is raised to 200° C. which is maintained for 4 hours. Stirring is terminated when the viscosity of the polymerizing mass becomes so great as to virtually prevent further stirring. The polymer is isolated, ground and dried in vacuum at room temperature. Some unreacted monomer is removed by heating the ground polymer at 80° C. and 110° C. for 16 hours each at a pressure of about 100 microns. A weight loss of 2.5% is observed. The resultant terpolymer has an inherent viscosity of 1.52 dl/g and comprises 9 mole percent lactide moieties and 81 mole percent glycolide moieties, the remainder being ethylene 1,4-phenylene-bis-oxyacetate moieties.

EXAMPLE 17

A flame dried 250 ml round bottom flask is charged under dry, oxygen-free conditions with amorphous, finely divided poly(ethylene 1,4-phenylene-bis-oxyacetate) (22.0 grams, prepared in the presence of 0.0044 weight percent dibutyltinoxide, inherent viscosity of 0.90 dl/g). The pressure is reduced, the flask immersed in silicone oil and heated at 40° C., 63° C., 77° C., 86° C., and 100° C. For 1 hour, ¾ hour, 1 hour, 1 hour, and 6 hours respectively to further dry and crystallize the resin. The flask is removed from the heat and allowed to cool. The cool flask is vented with nitrogen. Under dry, oxygen-free conditions, 91.1 grams glycolide is charged to the flask and the flask outfitted with an adaptor with hose connection and a dry mechanical stirrer.

After purging the reactor it is vented with nitrogen which is maintained at a pressure of one atmosphere throughout the remainder of the polymerization. The vessel is immersed in a preheated (70° C.) silicone oil bath. The temperature control of the bath is reset to 120° C. which is achieved in about 5 minutes and the glycolide becomes molten in about 25 minutes. The stirrer is partially lowered into the reactants and activated. After 5 minutes of gentle stirring at 120° C. the temperature controller is reset to 228° C. which is achieved in about 30 minutes. When the temperature reaches about 200° C. the stirrer is fully lowered into the reactants. A bath temperature of 228° C. is maintained for 2½ hours. The resultant polymer is isolated, ground and dried in a vacuum at room temperature. The inherent viscosity of the polymer is 1.10 dl/g.

Some unreacted glycolide is removed by heating the ground polymer at 110° C. and 0.1 mm Hg pressure for 16 hours. A weight loss of 1.2% is observed indicating a high degree of conversion. The resultant polymer comprises 90 mole percent (80.5 weight percent) glycolide moieties.

EXAMPLE 18

A flame dried 250 ml round bottom flask is charged under dry, oxygen-free conditions with divided bone-dry, poly(ethylene 1,3-phenylene-bis-oxyacetate) (22.0 g, prepared in the presence of 0.0071 weight percent dibutyltin oxide to an inherent viscosity of 0.84 dl/g) and glycolide (91.1 g., 0.785 moles). The flask is outfitted with an adaptor with hose connection and a dry mechanical stirrer assembly. After purging the reactor, it is vented with nitrogen which is maintained at a pressure of one atmosphere for the remainder of the run. The vessel is immersed in a silicone oil bath preheated to 70° C. which is achieved in the bath in about 5 minutes. In about 25 minutes the glycolide is melted and the stirrer is partially lowered into the reactants and activated. After 5 minutes of gentle stirring at 120° C. the temperature controller is reset to 225° C. which is achieved in about 25 minutes. When the temperature reaches 160° C. the stirrer is fully lowered into the reactants. A bath temperature of 225° C. is maintained for 2.5 hours. The polymer is isolated, ground, and dried under vacuum at room temperatures. The inherent viscosity of the polymer is 1.26 dl/g. Some unreacted glycolide is removed by heating the ground polymer at 110° C. and a pressure of 0.1 mm of mercury for 16 hours. A weight loss of 1.1% is observed indicating a high degree of conversion.

EXAMPLE 19

A polymerization is carried out as described in Example 18 except that the flask is charged with divided, bone-dry, poly(octa-methylene 1,4-phenylene-bis-oxyacetate) (29.3 g, prepared in the presence of 0.0054 weight percent dibutyltin oxide, inherent viscosity of 0.78 dl/g) and glycolide (91.1, 0.785 moles).

After polymerization the polymer is isolated, ground and dried under vacuum at room temperature. The polymer has an inherent viscosity of 1.21 dl/g.

EXAMPLE 20

A flame dried 250 ml round bottom flask is charged under dry, oxygen-free conditions with divided poly(-trans 1,4-cyclohexylenedicarbinyl 1,4-phenylene-bis-oxyacetate) (29.2 g. prepared in the presence of 0.0054 weight percent of dibutyltin oxide to an inherent viscosity of 0.93 dl/g). The pressure in the flask is reduced and the flask heated above room temperature to render the resin bone dry. After releasing with nitrogen, glycolide (91.1 g., 0.785 moles) is charged under dry, oxygen-free conditions. The reactor is outfitted with an adapter with hose connection and a dry mechanical stirrer assembly. After purging the reactor it is vented with nitrogen which is then maintained at one atmosphere pressure throughout the remainder of the run. The reactor is immersed in a silicone oil bath preheated to 70° C. The temperature controller is raised to 120° C. and the glycolide allowed melt. The stirrer is partially lowered into the reactants and activated. The temperature is raised to 230° C. and maintained at that temperature for 2 hours. When the temperature reaches 220° C. the stirrer is fully lowered into the reactants.

The polymer is isolated, ground and dried under vacuum at room temperature. The polymer has an inherent viscosity of 1.35 dl/g. Some unreacted glycolide is removed by heating the ground polymer at 110° C. at a pressure of 0.1 mm of mercury for 1.6 hours. A weight loss of 2.0% is observed indicating a high degree of conversion. The resultant polymer comprises 90 mole percent (75.7 weight percent) of glycolide moieties.

EXAMPLE 21

A flame dried 100 ml round bottom flask, outfitted with a vacuum tight stainless steel mechanical stirrer and a hose connection, is charged with 19.4 g. glycolide (0.167 moles) and 10.6 g. finely divided (passing a 10 mesh screen), amorphous, bone-dry poly(ethylene 1,4-phenylene-bis-oxyacetate) polyester resin (prepared in the presence of 0.02 weight percent dibutyltin oxide to an inherent viscosity of 0.91 dl/g). After purging the flask and venting with nitrogen, the flask is immersed in a silicone oil bath and connected to a gas supply to maintain nitrogen at one atmosphere of pressure. The mixture is heated to 120° C. to melt the glycolide and to swell and eventually dissolve the polyester resin. The temperature is increased to 170° C. and maintained for 20 hours (stirring is discontinued as the polymer becomes too viscous to stir) during which time the forming polymer crystallizes. The polymer is isolated, ground and dried under vacuum at room temperature. Some unreacted glycolide is removed by heating the ground polymer at 80° C. for 16 hours under vacuum: (a weight loss of 0.1% is observed). The devolatized polymer exhibits an inherent viscosity of 1.68 dl/g and 37% crystallinity (as measured by X-ray diffraction), a melting temperature of 224° C. (as measured by DSC, 20°

C./min. scan rate) and a composition (as determined by $^{13}$C NMR) of 20.1±0.9 mole percent (approximately 35.3 wt. percent) of ethylene 1,4-phenylene-bis-oxyacetate moieties and 79.9±0.9 mole percent (approximately 64.7 weight percent) of glycolide moieties.

The devolatilized polymer is extruded using an Instron Rheometer at a shear rate of 213 Sec.$^{-1}$ and 40 mil die. The extrudate is quenched in ice water and subsequently drawn in two stages; 6 times at 53° C. followed by 1.5 times at 70° C. The drawn fiber has a 5.3 mil diameter, a straight tensile strength of 123,000 psi, a knot tensile strength of 105,000 psi, an elongation at break of 20% and a Young's modulus of 1.81 million psi. The fiber is annealed under tension at 113° C. for 9 hours. The inherent viscosity of the annealed monofilament before and after gamma radiation sterilization at a dosage of 2.5 Mrads is 1.30 dl/g and 1.18 dl/g respectively.

In producing copolymers in accordance with this aspect of the invention, the poly(phenylene-bis-oxyacetate) is preferably hydroxyl-terminated, i.e., is made using a stoichiometric excess of the diol, but also should preferably have a sufficient molecular weight to limit the number of OH groups present in the polymerization reaction mixture, since these OH groups will determine the degree of polymerization. Preferably, the homopolymer has an inherent viscosity of at least 0.1 dl/g. In the event of having a low degree of polymerization homopolymer, a low molecular weight hydroxylic chain regulator such as glycolic acid or lauryl alcohol may be added. The desirable copolymers are those having an inherent viscosity of at least 0.3 dl/g measured at 25° C. at a concentration of 0.1 g/dl in hexafluoroisopropyl alcohol. Preferably the inherent viscosity of our new copolymers is from 0.6 to 1.6 dl/g or even a little higher. Wherever inherent viscosity is given throughout this specification, it has been determined in dl/g measured at 25° C. at a concentration of 0.1 g/dl in hexafluoroisopropyl alcohol.

In producing the copolymers described above, the original poly(phenylene-bis-oxyacetate) does not maintain its original length, and the glycolate moieties become incorporated into the poly(phenylene-bis-oxyacetate) polymer chain to produce short sequences of the poly-oxyacetate polymer connected by the polyglycolate chains. The relative length of the two polymer segments is determined by the composition of the original reaction mixture and by the reaction conditions. By placing our new stabilizing units of the poly(phenylene-bis-oxyacetate) throughout the polyglycolic acid, our new polymer is stabilized against high-energy radiation such as gamma irradiation with a $^{60}$Co source, and radiation sterilizable absorbable materials are produced.

In producing these various copolymers the glycolide reacts with our new homopolymer or it reacts with a mixture of diol and the monomer in a random fashion to obtain the absorbable materials described. The copolymers have better mechanical properties, tensile strength, and faster absorption than the less regular copolymers. This would be as expected as the more polyglycolic acid present in the polymer the more absorbable the final products will be.

The copolymers made in accordance with this aspect of the invention i.e., from homopolymer and glycolide and/or lactide, preferably have less than about 40 weight percent of the poly(phenylene-bis-oxyacetate) moieties and more than about 60 weight percent of the glycolide moieties.

These copolymers are especially suitable for making fabricated, absorbable, sterilized surgical devices having good strength, since the copolymers are readily oriented. Hence, these copolymers are especially adapted to being used to make sterile surgical sutures, especially such sutures with attached needles.

The copolymers comprising from about 41 to 79 weight percent of the poly(phenylene-bis-oxyacetate) moieties and from about 21 to 59 weight percent of the glycolide moieties while not particularly suitable for producing high strength, oriented suture materials, are useful in producing high-energy radiation sterilizable, absorbable molded surgical devices.

The fiber-forming polymers of the invention can be used in the production of reinforcing fibers for partially or fully absorbable composites that are used for supporting implants and prosthetic devices. The polymers of the invention can also be used in powdered form as absorbable fillers in partially or fully absorbable implants or prosthetic devices.

PREPARATION OF RANDOM COPOLYMERS

The random copolymers of the invention are radiation sterilizable random copolymers that are represented by Formula IV:

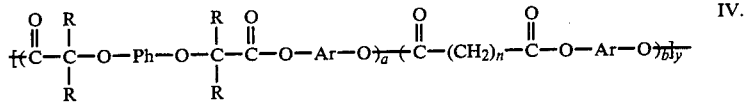

wherein Ar represents 1,3- or 1,4-phenylene, wherein Ph and R are as defined above with respect to Formula I, wherein n is a number having an average value of from 4 to 10, wherein a and b are numbers whose average values reflect the proportions of the two components of the polymer, and wherein y is a number whose average value reflects the degree of polymerization resulting in a solid polymer having an inherent viscosity of at least 0.3 dl/g measured at 25° C. at a concentration of 0.1 g/dl in hexafluoroisopropyl alcohol. Generally, these polymers are formed by reacting hydroquinone diacetate with sebacic acid and our new phenylene-bis-oxyacetate monomers. The following are specific examples for producing such copolymers.

EXAMPLE 22

A 100 ml stirred reactor, suitable for polycondensation reactions, is charged with 1,4-phenylene-bis-oxyacetic acid (3.6 g, 0.0159 moles), sebacic acid (3.3 g, 0.0163 moles), hydroquinone diacetate (6.5 g, 0.0335 moles) and dibutyltin oxide (4.2 mg, 0.027 mmoles). The reactor is purged and vented with nitrogen and immersed in a silicon oil bath and heated (under an atmosphere of nitrogen) to and maintained at 235° C. for 5 hours. The acetic acid formed during the polymerization is collected and removed. The pressure is reduced to about 100 microns of mercury and heating is continued for an additional 3 hours at 235° C. while continuing to remove distillates. The resulting polymer possesses an inherent viscosity in HFIP of 0.59 dl/g.

EXAMPLE 23

A 100 ml stirred reactor suitable for polycondensation reactions, is charged with 1,4-phenylene-bis-oxyacetic acid (6.0 g., 0.026 moles), sebacic acid (2.7 g., 0.013 moles), adipic acid (1.9 g., 0.013 moles), hydroquinone diacetate (10.8 g., 0.0557 moles), and dibutyltin oxide (6.6 mg., 0.027 mmoles). The reactor is purged and vented with nitrogen and immersed in a silicone oil bath and heated (under an atmosphere of nitrogen) to and maintained at 235° C. for 3 hours. The acetic acid formed during the polymerization is collected and removed. The pressure is reduced to about 100 microns of mercury and heating is continued for an additional 3 hours at 235° C. while removing distillates. The resulting polymer is insoluble in hexafluoroisopropyl alcohol. The polymer is 40% crystalline (as measured by X-ray diffraction) and exhibited a Tm of 225° C. (as measured by DSC). Monofilament fiber of the terpolymer is found to lose 47% of its weight after boiling for 23 hours in a 7.25 buffer solution.

The resulting polymer is a slow absorbing material and can be melt processed. It is crystalline and can be used to produce surgical devices which are sterilizable with high-energy radiation.

PRODUCTION OF STERILIZABLE SURGICAL DEVICES

The following examples are provided to show the various desirable properties of surgical sutures and other surgical devices made with the new polymers of the present invention. In these examples, various parameters such as strength and absorption characteristics and the like have been measured. These measurements are made in accordance with the following tests:

GENERATION OF ABSORPTION DATA

Under aseptic conditions; two 2-centimeter segments of a suture sample are implanted into the left and right gluteal muscles of female Long-Evans rats. Two rats per period are implanted for each of the examination periods. The animals utilized in these studies are handled and maintained in accordance with the requirements for the Animal Laboratory Welfare Act and its 1970 Amendment. The rats are killed at the appropriate periods by carbon dioxide asphyxiation then their gluteal muscles excised and fixed in buffered formation. Utilizing standard histologic techniques, H and E stained slides of the muscles and implanted sutures are prepared for microscopic examination. Utilizing an ocular micrometer, the approximate suture cross-sectional area is estimated in each site. The cross-sectional area at five days is used as the reference value for estimating percent cross-sectional area remaining at subsequent intervals.

Tissue responses to the implanted sutures are determined according to the following method. A method modified from that described by Sewell, Wiland and Craver (Surg., Gynecol., and Obstet., 100:483:494, 1955) is utilized to assess responses to implanted sutures. In this method the width of the reaction zone measured along the radius from the center of the suture cross-section is graded as follows:

|  | Assigned Grade |
|---|---|
| 0 to 25 microns | 0.5 |
| 25 to 50 microns | 1.0 |
| 50 to 200 microns | 2.0 |
| 200 to 400 microns | 3.0 |
| 400 to 600 microns | 4.0 |

Cellular response is graded from 0 to 4 based on increasing concentrations of cells in the reaction zones. A grade of 0.5 is assigned where only a few cells are widely scattered in the reaction zone while a grade of 4 is assigned where high cellular concentration is present in the site.

Weighting factors are assigned to zone of reaction and inflammatory cells in computing reaction score as follows:

| Characteristic | Weighting Factor |
|---|---|
| Width of Zone | 5 |
| Overall Cell Density | 3 |
| Neutrophils | 6 |
| Giant Cells | 2 |
| Lymphocytes/Plasma Cells | 1 |
| Macrophages | 1 |
| Eosinophils | 1 |
| Fibroblasts/Fibrocytes | 1 |

A sample score is computed as follows:

| Parameter | Grade × | Weighting Factor = | Score |
|---|---|---|---|
| Zone | 2 | 5 | 10 |
| Cell Density | 2 | 3 | 6 |
| Macrophages | 2 | 1 | 2 |
| Giant Cells | 1 | 2 | 2 |
| Fibroblasts | 2 | 1 | 2 |
|  |  |  | 22 |

Adjetival ratings assigned to reaction scores are arbitrarily assigned within the following limits: 0-none; 1-8 minimal; 9-24 slight; 25-40 moderate; 41-56 marked; over 56 extensive.

Elongation and Modulus are determined by standard Instron testing methods used in the industry.

Breaking Strength Retention:

The breaking strength of a sample is determined by implanting two strands of a sample in the dorsal subcutis of each of twelve (12) Long-Evans rats. Thus 24 strands of each sample are implanted corresponding to the three implantation periods; eight examples of each sample for each of the periods. The periods of in vivo residence are 7, 14, and 21 days. The ratio of the mean value (of 8 determinations) of the breaking strength (determined with an Instron Tensile tester in accordance with standard testing procedure) at each period to the mean value (of 8 determinations) obtained for the sample prior to implantation constitutes its breaking strength for that period.

Most of the polymers described in this invention can readily be extruded in an Instron Capilliary Rheometer or screw-type extruder at temperatures usually exceeding the polymer melting temperature by 10° to 70° C. The resulting extrudate can be drawn in a one or two stage process using a set of hot rollers or a glycerine bath or a combination. The draw ratio may vary from about 300–900%. Some of the polymers of this invention will produce oriented fibers exhibiting exceptional tensile properties. Typical 8-10 mil. strands of these materials may possess knot tensiles in the $40-120\times10^3$ PSI range with straight tensiles in the $50-170\times10^3$ PSI range and a Young's modulous of more than $10^6$ PSI. Depending on the composition, elongation at break ranges from about 3 to 30%. The in vitro and in vivo absorption data of typical polymers indicate their tendency to absorb when used as surgical devices in 90 days to over 1 year. The polymers of the present invention lend themselves to ready extrusion as strong fibers useful in the production of absorbable monofilament sutures. The polymers of the present invention may be used to produce extremely small size sutures such as those used in opthalmic surgery. The monofilaments may be annealed at between 60° C. and 130° C. for from 2 to 20 hours to improve their tensile properties and conventional stability; the conditions depending on the particular polymer and obtainable by experimentation.

EXAMPLE 24

A polymer made as described in Example 15 is melt spun in an Instron Rheometer at 245° C. employing a 40 mil die with an L/D ratio of 24 and a sheer rate of 213 sec$^{-1}$. The extrudate is taken up through ice water and subsequently drawn in a glycerine draw bath in two stages. The first stage is drawn 5× at 49° C. followed by a draw of 1½× at 92° C. Inherent viscosity of the extrudate is found to be 1.52 dl/g measured at 25° C. at a concentration of 0.1 g/dl in hexafluoroisopropyl alcohol. The drawn fibers are determined to be 33% crystalline and upon annealing under tension at 112° C. for 9 hours are found to be 36% crystalline. The final fiber has a diameter of 7.0 mil. The properties of the fibers are provided in the following table:

|  | DRAWING 5× | DRAWING 5× FOLLOWED BY 1.5× | DRAWN FIBER AFTER ANNEALING |
|---|---|---|---|
| TENSILE STRENGTH PSI | 120,700 | 172,000 | 174,000 |
| KNOT TENSILE STRENGTH PSI | 73,400 | 104,000 | 117,000 |
| ELONGATION AT BREAK | 53% | 12% | 11% |
| MODULUS $10^6$ PSI | 0.77 | 1.71 | 2.42 |

EXAMPLE 25

Polymers made and described in conjunction with Example 15 are extruded through a clean extruder using a 12 mil, 16 hole die with the application of a spin lubricant to produce 7000 yards of 56.8 gram denier yarn (3.55 denier per filament). The extrusion conditions were as follows:

Melt temperature in block: 500° C.
Melt temperature in die: 510° C.
Chimney air temperature: 520° C.
Throughput: 485 grams per hour Orientation at a draw ratio of 5× with a feed roll temperature of 155° C. and an annealing roll temperature of 195° F. is used.

The yarn is assembled into braid made up of three core threads, 16 filaments each and 16 carrier threads, 16 filaments each. The braid is hot stretched and annealed under tension. The braid denier is 1072 grams. The diameter is 13.5 mils. The braid has an elongation at break at 23%, a straight tensile strength of 106,600 PSI and a knot tensile strength of 67,100 PSI. A sample of polyglycolic acid is similarly extruded, braided and post-treated for use as a control. Portions of the braid are cut to appropriate lengths, placed in individual paper folders and vented foil, heat sealable envelopes. The braids are sterilized by gamma irradiation by using standard industrial conditions. The physical properties of both braids are determined and the results are given in the following table:

|  | Polymer of the Invention Before Irradiation (Exp. 15) | Polymer of the Invention After (2.89 Mrads) of Irradiation (Exp. 15) | Polyglycolic Acid Before Irradiation | Polyglycolic Acid After 2.76 Mrads of Irradiation |
|---|---|---|---|---|
| Diameter (Mils) | 13.6 | 13.4 | 14.1 | 14.2 |
| Straight Tensile ($10^3$ PSI) | 105.9 | 100.0 | 130.7 | 113.2 |
| Knot Tensile ($10^3$ PSI) | 65.0 | 61.2 | 74.0 | 59.7 |
| ELONGATION AT Break (%) | 24 | 22 | 19 | 16 |

The absorption characteristics of both the braid of the invention and the polyglycolic acid control are determined. The results are given in the following table:

| Percent Cross-sectional Area Remaining | | | | | |
|---|---|---|---|---|---|
| | Days Post Implantation | | | | |
| | 5 | 70 | 91 | 119 | 182 |
| Braid of the present Invention Irradiated at 2.89 Mrad (Exp. 15) | 100 | 92 | 49 | 1 | 0 |
| Polyglycolic Acid Braid irradiated at 2.76 Mrad | 100 | 59.5 | 19.5 | 3 | 0 |

The braided samples of the invention elicited tissue response scores in the slight range with some zero scores at the 91 and 119 day periods.

The average breaking strength values after 7 continuous implantations in rats is determined on both the braid of the invention (Example 15) and the polyglycolic acid control braid. The following table gives the results of these tests:

|  | Time in Days | | | |
|---|---|---|---|---|
|  | 0 | 7 | 14 | 21 |
| Braid of the Invention Non-Irradiated (Exp. 15) | | | | |
| Lbs. | 9.51 | 11.63 | 9.96 | 9.23 |
| % | 100 | 122 | 105 | 97 |
| Braid of the Invention Irradiated 2.89 Mrads (Exp 15) | | | | |
| Lbs. | 9.43 | 10.63 | 8.25 | 6.76 |
| % | 100 | 113 | 88 | 72 |
| Braid of the Invention Irradiated | | | | |

5 Mrads (Exp. 15)

| | Time in Days | | | |
|---|---|---|---|---|
| | 0 | 7 | 14 | 21 |
| Lbs. | 8.58 | 9.44 | 7.88 | 4.71 |
| % | 100 | 110 | 92 | 55 |
| Polyglycolic Acid Non-Irradiated | | | | |
| Lbs. | 13.41 | 15.06 | 9.90 | 6.85 |
| % | 100 | 112 | 74 | 51 |
| Polyglycolic Acid Braided Irradiated at 2.75 Mrads | | | | |
| Lbs. | 12.76 | 11.06 | 4.91 | 0.00 |
| % | 100 | 87 | 38 | 0 |
| Polyglycolic Acid Braid Irradiated at 5.33 Mrads | | | | |
| Lbs. | 12.91 | 9.70 | 2.04 | 0.00 |
| % | 100 | 75 | 16 | 0 |

Typical fiber grade polymers of the invention can readily be spun using a screw type extruder with a multi-hole die at temperatures usually exceeding the polymer melting temperature by about 10° C. to 70° C. With the aid of a spin lubricant, the extrudates may be drawn to produce multifilament yarn with a desirable denier per filament of from 1 to 5. The multifilament yarn can be braided, hot stretched and scoured to provide desirable sizes of braided sutures in the sizes of 2 to 8.0. For further improvement in suture tensile properties and dimensional stability the sutures may be annealed at 60° to 150° C. from about 2 to 20 hours.

Typical molding grade polymers of the invention can readily be injection or compression molded at temperatures usually exceeding the polymer temperature by from 10° C. to 60° C.

Absorbable sutures and other absorbable products made from polymers containing phenylene-bis-oxyacetate moieties as an inherent part of the chains may be sterilized at a dose of about 2.5 Mrads. of gamma radiation using a cobalt 60 source. A minimal loss in physical properties as judged by comparison of inherent viscosity, tensile strength and in vivo strength with control materials not exposed to cobalt is observed. This unexpected retention of physical properties in our new polymers presents a distinct advantage over commercially available synthetic, absorbable sutures which undergo significant deterioration upon sterilization with high energy radiation.

The polymers of the invention can be readily dyed either by adding the dye during polymerization or in the extrusion melt using conventional disperse dyes such as D&C violet #2 and D&C Green #6. Solubility of these dyes in the partially aromatic polymers and their associated dye retention allow the use of disperse dyes at different concentrations to give desired color intensities for different shaped articles.

Suitable coatings can be applied to braided sutures made from the polymers of this invention to improve the handling and tiedown characteristics and reduce tissue damage upon suturing and improve knot security as well as minimize the capillarity of the braid and probability of infection. The coatings may be of an absorbable, low melting, low degree of polymerization type of alkylene oxalate copolymers and may be applied by suitable techniques. A composite coating made of calcium stearate and 65/35 poly(1(—)lactide-co-glycolide) may also be supplied by a suitable technique to the braided suture.

While many of the preceding examples are directed to the preparation of sutures and monofilament sutures, the various new polymers of the invention may also be used in the manufacture of other suture constructions of both the single and multi-filament configurations and may also be used in preparation of surgical fabrics and/or welded synthetic devices such as veins and arterial grafts. In addition, our new materials may be used to make various molded products, such as orthopedic pins, screws, plates, and clamps, clips, staples, hooks, snaps; various bone substitutes such as prostheses; needles; interuterine devices; various capillaries such as urether ducts, etc.; various vascular implants, couplers or supports, vertebral discs and the like.

Having now described the invention it will be understood by those skilled in the art that variations and modifications of the specification described above may be employed without departing from the spirit and scope of the present invention as defined in the appended claims.

What we claim is:

1. A radiation sterilizable, absorbable polymer of the formula:

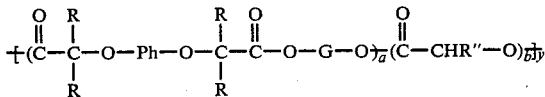

wherein G represents the residue after removal of the hydroxyl groups of a dihydric alcohol, said dihydric alcohol being selected from the group consisting of $C_2$ to $C_{16}$ alkylene glycols, polyalkylene glycols, 1,4-cyclohexanedimethanol, and 1,4-bis(2-hydroxyethoxy)-benzene, wherein Ph represents 1,2-, 1,3-, or 1,4-phenylene, wherein R represents hydrogen or lower alkyl, wherein R" represents hydrogen or methyl, wherein a and b represents numbers whose average values represent the proportions in the copolymer of the two units in the parentheses, and wherein y represents a number whose average value represents the degree of polymerization resulting in a solid polymer.

2. The polymer of claim 1 wherein G is cyclohexylene dimethylene or alkylene of from 2 to 16 carbon atoms, and wherein each R is hydrogen.

3. The polymer of claim 2 wherein G is alkylene of from 2 to 6 carbon atoms.

4. The polymer of claim 3 wherein R" is hydrogen.

5. The polymer of claim 2, 3, or 4 wherein Ph is 1,4-substituted.

6. The polymer of claim 5 wherein G is ethylene.

7. A radiation sterilizable absorbable surgical device comprising a copolymer of the formula:

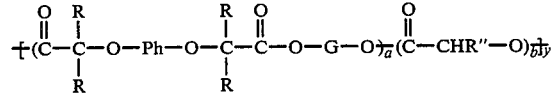

wherein G represents the residue after removal of the hydroxyl groups of a dihydric alcohol, said dihydric alcohol being selected from the group consisting of $C_2$ to $C_{16}$ alkylene glycols, polyalkylene glycols, 1,4-cyclohexanedimethanol, and 1,4-bis(2-hydroxyethoxy)-benzene, wherein Ph represents 1,2-, 1,3-, or 1,4-phenylene, wherein R represents hydrogen or lower alkyl, wherein R" represents hydrogen or methyl, wherein a and b represents numbers whose average values represent the proportions in the copolymer of the two units in the parentheses, and wherein y represents a number whose average value represents the degree of polymerization resulting in a solid polymer having an inherent viscosity of at least 0.3 dl/g measure at 25° C. at a concentration of 0.1 g/dl in hexafluoroisopropyl alcohol.

8. The device of claim 7 wherein the copolymer has the formula:

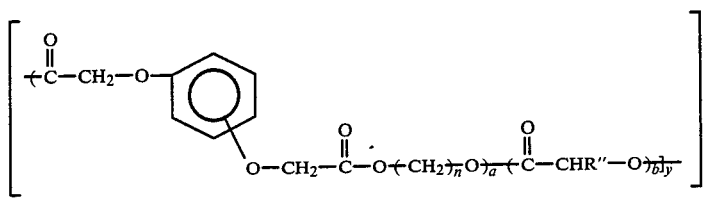

where n is a number having a value of from 2 to 6.

9. The device of claim 7 or 8 wherein the device is a surgical suture.

10. The device of claim 9 wherein the suture has a needle attached to one end of the suture.

11. A device according to claim 8, 9, or 10 which device has been sterilized by gamma irradiation using a cobalt 60 source.

12. A process for producing the radiation sterilizable, absorbable, normally solid, copolymer of claim 1, which process comprises reacting a mixture of phenylene-bis-oxyacetate of the formula:

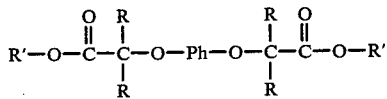

wherein R and Ph are as defined in claim 1, and wherein each R' individually is lower alkyl or phenyl, with a glycolide and a dihydric alcohol in the presence of a suitable catalyst at an elevated temperature under an inert atmosphere and for a sufficient period of time to produce a solid polymer having an inherent viscosity of at least 0.3 dl/g measured at 25° C. at a concentration of 0.1 g/dl in hexafluoroisopropyl alcohol.

13. A process for preparing a radiation sterilizable, absorbable, normally oil, essentially random copolymer of the formula:

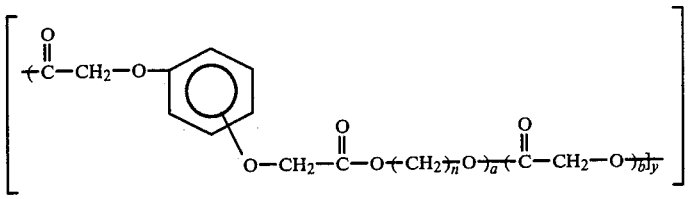

wherein n is 2 to 6, the benzene ring is 1,2-, 1,3-, or 1,4-substituted, a and b are numbers having average values such that the short chain units represented by b comprise less than 20% by weight of the polymer, and y is a number whose average value represents the degree of polymerization, comprising: reacting a mixture of dimethyl phenylene-bis-oxyacetate, glycolide, and $C_2$ to $C_6$ alkylene glycol in the presence of a suitable catalyst, at a temperature of from 120° C. to 240° C. under a nitrogen atmosphere for a sufficient period of time to produce a solid polymer having an inherent viscosity of 0.3 dl/g measure at 25° C. At a concentration of 0.1 g/dl in hexafluoroisopropyl alcohol.

14. The process according to claim 13 wherein the mixture is further heated to a temperature of from 160° C. to 240° C. at a reduced pressure of less than 5 mm. of mercury.

15. The process according to claim 13 or 14 wherein the catalyst is dibutytin oxide or stannous octoate.

16. The process according to claim 15 where the dimethyl phenylene-bis-oxyacetate is the para-isomer.

17. A process for producing the radiation sterilizable, absorbable, normally solid, copolymer of claim 1, which process comprises reacting the polymer of claim 7 with glycolide or a mixture of glycolide and lactide at an elevated temperature for a period of time sufficient to produce a solid polymer having an inherent viscosity of at least 0.3 dl/g measured at 25° C. at a concentration of 0.1 g/dl in hexafluoroisopropyl alcohol.

18. A process for producing a radiation sterilizable, absorbable, normally solid, copolymer of the formula:

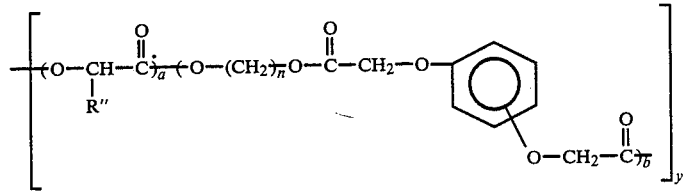

where R" is H or $CH_3$, the benzene ring is 1,3- or 1,4-substituted, n is 2 to 6, a and b are numbers whose average values are such that the repeat units represented by a comprise more than 60% by weight of the polymer, and y is a number having an average value that reflects the degree of polymerization, comprising: reacting a phenylene-bis-oxyacetate of the formula:

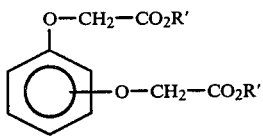

where R' is lower alkyl or phenyl and the benzene ring is 1,3- or 1,4-substituted, with $C_2$ to $C_6$ alkylene glycol in the presence of a suitable catalyst at a temperature of about 120° C. to about 220° C. and in an inert atmosphere, continuing the reaction at a temperature of about 160° C. to about 240° C. and a reduced pressure, adding glycolide or a mixture of glycolide and lactide to said reaction and continuing said reaction at a temperature of from 140° C. to 240° C. for a period of time sufficient to produce a solid polymer having an inherent viscosity of at least 0.3 dl/g measured at 25° C. at a concentration of 0.1 g/dl in hexafluoroisopropyl alcohol.

19. A process according to claim 18 wherein the catalyst is dibutyltin oxide or stannous octoate.

20. A process according to claim 19 wherein the phenylene-bis-oxyacetate is dimethyl phenylene-bis-oxyacetate.

21. A process according to claim 18 or 19 wherein the reduced pressure is less then 5 mm. of mercury.

22. A process according to claim 18 wherein the reaction is continued at a temperature of greater than 225° C. for a period of time sufficient to produce a solid polymer having an inherent viscosity of at least 0.6 dl/g measured at 25° C. at a concentration of 0.1 g/dl in hexafluoroisopropyl alcohol.

23. A radiation sterilizable, absorbable normally solid copolymer of the formula:

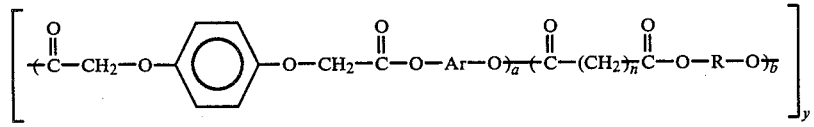

where Ar is 1,3 or 1,4 phenylene, n has an average value of 4 to 10, a and b are numbers such that repeat units represented by b are 1 to 50 percent by weight of the copolymer, and y is a number whose average value reflects the degree of polymerization resulting in a solid polymer having an inherent viscosity of at least 0.3 dl/g measured at 25° C. at a concentration of 0.1 g/dl in hexafluorisopropyl alcohol.

24. The copolymer of claim 23 wherein n is 8.

25. A surgical device comprising the copolymer of claim 23.

26. A device according to claim 25 wherein the device is a surgical suture.

27. A suture according to claim 26 having a needle attached to one end of the suture.

28. A suture according to claim 26 or 27 which has been sterilized by gamma irradiation using a cobalt 60 source.

29. A process for producing the radiation sterilizable, absorbable, normally solid copolymer of claim 23 comprising reacting a phenylene-bis-oxyacetate of the formula:

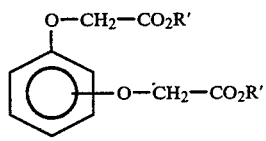

wherein R' is lower alkyl or phenyl and the benzene ring is 1,2-, 1,3-, or 1,4-substituted, with an aliphatic diacid or mixture thereof and hydroquinone diacetate or resorcinol diacetate in the presence of a suitable catalyst and at a temperature of from 200° C. to 280° C. for a sufficient period of time to produce a solid polymer having an inherent viscosity of at least 0.3 dl/g measured at 25° C. at a concentration of 0.1 g/dl in hexafluoroisopropyl alcohol.

30. The process according to claim 29 wherein the phenylene-bis-oxyacetate is dimethyl phenylene bis-oxyacetate.

31. The process according to claim 29 or 30 wherein the benzene ring is 1,4-substituted.

32. The process according to claim 31 wherein the aliphatic acid is sebacic acid.

33. The process according to claim 29 wherein the catalyst is dibutyltin oxide or stannous octoate.

34. A surgical device comprising the radiation sterilizable, absorbable polymer of claim 1.

* * * * *

UNITED STATES PATENT AND TRADEMARK OFFICE
CERTIFICATE OF CORRECTION

PATENT NO. : 4,689,424

DATED : August 25, 1987

INVENTOR(S) : Shalaby W. Shalaby et al.

It is certified that error appears in the above-identified patent and that said Letters Patent is hereby corrected as shown below:

Column 26, line 2

"oil"

should read

--solid--

Signed and Sealed this

Twenty-second Day of December, 1987

Attest:

DONALD J. QUIGG

Attesting Officer

Commissioner of Patents and Trademarks